US008936549B2

(12) United States Patent
Cobb et al.

(10) Patent No.: US 8,936,549 B2
(45) Date of Patent: Jan. 20, 2015

(54) APPARATUS AND METHOD FOR RETRACTION OF TISSUE

(75) Inventors: Tyson Cobb, Bettendorf, IA (US); Alejandro Badia, Miami, FL (US); Stacey Berner, Reistertown, MD (US); Stephen Topper, Colorado Springs, CO (US); Vincent van Donck, San Diego, CA (US)

(73) Assignee: American Hand Institute, LLC, Rochester, NY (US)

( * ) Notice: Subject to any disclaimer, the term of this patent is extended or adjusted under 35 U.S.C. 154(b) by 361 days.

(21) Appl. No.: 12/874,536

(22) Filed: Sep. 2, 2010

(65) Prior Publication Data

US 2011/0054262 A1 Mar. 3, 2011

Related U.S. Application Data

(60) Provisional application No. 61/275,785, filed on Sep. 2, 2009.

(51) Int. Cl.
*A61B 1/32* (2006.01)
*A61B 17/02* (2006.01)
*A61B 1/00* (2006.01)

(52) U.S. Cl.
CPC ............ *A61B 17/02* (2013.01); *A61B 1/00147* (2013.01)
USPC ........... 600/210; 600/213; 600/214; 600/215; 600/217; 600/235

(58) Field of Classification Search
USPC ......... 600/206, 208, 210, 214–215, 217, 235, 600/238, 239
See application file for complete search history.

(56) References Cited

U.S. PATENT DOCUMENTS

| | | | | |
|---|---|---|---|---|
| 3,731,673 | A * | 5/1973 | Halloran | 600/210 |
| 5,303,694 | A * | 4/1994 | Mikhail | 600/214 |
| 5,520,610 | A | 5/1996 | Giglio et al. | |
| 6,074,343 | A | 6/2000 | Nathanson et al. | |
| 6,409,731 | B1 | 6/2002 | Masson et al. | |
| 7,022,069 | B1 | 4/2006 | Masson et al. | |
| 2009/0182203 | A1* | 7/2009 | Hartnick et al. | 600/219 |

* cited by examiner

*Primary Examiner* — Andrew Yang
*Assistant Examiner* — Olivia C Chang
(74) *Attorney, Agent, or Firm* — Joseph R. Englander; Shutts & Bowen LLP

(57) ABSTRACT

A self-retaining retractor and surgical method of retracting integument at a surgical site comprising a medial arm moveably connected to a first end of an extension arm. The extension arm is connected to a lateral arm. The connection may be made after the medial arm is in the surgical site. The extension arm may be moved from an undeployed position to a deployed position. The medial arm or the lateral arm may include a surgical instrument holder, such as a holder for an endoscope. A locking mechanism may be used to lock the retractor in a deployed position. A strap may also be used to secure the retractor.

2 Claims, 10 Drawing Sheets

APPARATUS AND METHOD FOR RETRACTION OF TISSUE

CROSS-REFERENCE TO RELATED APPLICATIONS

This application contains subject matter that is common to, and is a non-provisional application of, U.S. Provisional Patent Application Ser. No. 61/275,785, entitled "AN APPARATUS FOR RETRACTION OF TISSUE FOR AND DURING SURGICAL PROCEDURES AND PROCESS FOR MAKING SAME", filed Sep. 2, 2009, which application is incorporated by reference herein in its entirety. This application claims priority under 35 U.S.C. §119(e) as to common subject matter.

BACKGROUND OF THE INVENTION

1. Field of Invention

The present invention relates to surgical procedures and apparatus, and more specifically to a self-retaining retractor and surgical method of using a self-retaining retractor at a surgical site.

2. Background of Invention

Surgical "retraction" is the drawing back of body tissue. When a surgical procedure involves making an incision, the incision site itself often must be retracted in order for the surgery to proceed through completion. During surgery, internal organs, bones, and tissues are intermittently retracted through the opening created in the retracted incision site.

In certain surgeries, an assistant's fingers are used as retractor paddles to hold the site of the incision open. However, greater technical ease is available through the use of various mechanical retractor systems. Such mechanical retractor systems can be divided into two major groups: externally mounted "fixed" to the operating table and self-retaining retractors.

Mechanical systems attached to the operating table present the same type of physical obstruction to the movements of the surgeon as presented by the assistant's body, arms, and hands since the externally fixed retractor system consists of a vertical column, supporting ring or arms and retractor paddles attached thereto. All components of the fixed retractor system are adjustable in multiple planes and axes of motion. These components, however, are not independently adjustable in the vertical plane; movement of a ring or support arm of the fixed retractor system necessitates movement and adjustment of all retractor paddles attached thereto.

Ideally, mechanical tissue retractors, both externally mounted and self retaining, need to provide for internal organ, bone, and tissue retraction. Both types of retractor systems need to be quickly and easily assembled, positioned, and repositioned in all planes and axes of motion, and present as little obstruction as possible to the surgeons movements and line of sight. Both types of retractor systems must protect the sterile field, diminish the risk of tissue trauma and still remain sufficiently stable to function properly without the need for assistance.

Self-retaining retractors have attempted to provide for internal organ and tissue retraction through the open incision, but have failed to permit quick, independent, easy and safe adjustment of internal organ and tissue retractor arms in all planes and axes of motion. Furthermore, self-retaining retractors have failed to provide an internal support mechanism for bone, organs, and tissue within the incision site, making the prior art ineffectual, unsafe, or both. Existing self-retaining retractors are not readily or easily adjustable in the vertical plane and must traverse through or over internal tissue before reaching the optimal location for the surgical procedure.

Various patents have issued relating to surgical retractors. U.S. Pat. No. 5,520,610 issued to Giglio on May 28, 1996 describes a self-retaining retractor that includes flexible, resilient retractor paddles which can be placed into the incision. A rigid frame includes two interlocking halves that lay over the incision longitudinally. The incision retractor paddles are manually clipped to each frame half and the frame halves may then be opened to the extent of tissue retraction desired.

U.S. Pat. No. 6,074,343 issued to Nathanson et al. on Jun. 13, 2000 describes a surgical incision retractor to be used in small tissue incisions and includes a plurality of blades that can be operated simultaneously or at least one or more blades can be operated independently. Right and left retractor blades are mounted on an actuator mechanism that spreads or expands the blades as a rotatable primary actuator knob is rotated. A third retractable arm is mounted for simultaneous operation with the right and left retractor blade or independent operation through a secondary rotatable actuator knob that extends or retracts a threaded shaft attached to the center retractor blade.

U.S. Pat. No. 7,022,069 issued on Apr. 4, 2006 to Masson and Henry describes a circumferential retractor apparatus including a first retractor paddle, a second retractor paddle and an elastic member. Each of the first and second retractor paddles includes a body portion with an arm extending outwardly therefrom. The arm supports a grasping surface. The arm of the retractor paddle has a hole formed therein through which the elastic member passes.

On Jun. 25, 2002, Masson and Henry were granted U.S. Pat. No. 6,409,731 describing a bone leveler or apparatus that includes a first blade member having a forward end suitable for contacting the bone and a rearward end, a second blade member having a forward end suitable for contacting the bone and a rearward end, and an elastic member having one end received by the first blade member and an opposite end received by a second blade member. Each of the blade members has an identical configuration. Each of the blade members has a hole formed between the forward end and rearward end. The elastic member has one end received by the hole of the first blade member and an opposite end received by the hole of the second blade member.

A typical procedure generally involves an operating team of trained practitioners that includes a surgeon and at least one assistant or more, depending on the complexity of the operation. Once an operation site is sterile, as recommended, and the operating team and patient prepped, a surgeon will usually make a predetermined incision of integument, such as skin, in order to view and access a predetermined region of the patient's body.

A tool typically used in the medical field to create and maintain an aperture is commonly referred to as a retractor. A basic retractor comprises a blunt object—or other form object that will not perforate, deform, or compromise an incised edge—and is generally referred to as an paddle or arm (as referenced herein). The arm may be similar in width to the width of an incision and of a length sufficient to be inserted through an incision to a desired depth of a patient's body while capable of being manipulated from outside the patient's body. Force is usually applied to a portion of an inserted arm, distal to incised edges, which causes integument to separate or retract, thus forming an aperture.

Depending on the degree of surgical procedure that is performed, an aperture may need to be maintained for a short period of time or for hours. It is not uncommon for a practitioner to use a finger as an arm or other object to retract and retain integument. This practice requires constant manual/physical force and can be undesirable because the finger may obstruct a surgeon's view, may fatigue, or may be distracted and move which can result in injury to a practitioner or patient. Therefore, when manual retractors are avoided, practitioners may use mechanical arms to separate integument and maintain an aperture.

Mechanical retractors generally involve connecting an arm to a stationary object outside the incision, like an operating table, hanger, or frame supported by a patient. This type of retractor has been known to cause obstruction to practitioners and even injury to a patient if they move during surgery or when a time consuming disassembly is required in an emergency situation.

SUMMARY OF THE INVENTION

The aforementioned shortcomings of retractors have been addressed by the present invention. In accordance with an aspect of the present invention, a self-retaining retractor and surgical method of retracting integument at a surgical site is disclosed.

In an embodiment of the retractor of the present invention, a medial arm is moveably connected to the first end of an extension arm. Both arms are substantially planar in a closed position to provide for minimal impedance to integument when inserted into an incision. A lateral arm connects to the second end of the extension arm such that when force is applied to the lateral arm in a general subdermal direction, the extension arm is driven out of plane with the medial arm. The lateral arm may then pivot about its axis with the extension arm away from the medial arm, thereby causing the incision to open and forming an aperture. Arms may thereafter be locked relative to each, in order to provide a self-retained retraction of an incision site for the duration of a surgical procedure. Once the retractor is locked in place, practitioners' hands are free so that the surgeon may concentrate on using them for the procedure, which may allow a procedure to be performed using a smaller team, thereby minimizing the number of surgical tools required, reducing risks of injury to patients and practitioners, reducing labor costs, and lowering the potential for infections to the patient and violations of the sterile field by practitioners.

In another embodiment of the invention, the dimensions of one arm may be the same or different from dimensions of another arm, in order to accommodate variable visualization and exposure requirements according to a procedure.

An object of the invention is to provide a self-retaining retractor and method of use for surgical procedures.

Another object of the invention is to provide a self-retaining retractor and method of use for superior visualization of an incision site without interference from practitioner hands, which otherwise may obstruct a practitioner's view or block light.

It is another object of the invention to provide a self-retaining retractor and method of use for optimal visualization of an incision site without hands-on manipulation of a retractor.

It is a yet another object of the invention to provide a self-retaining retractor and method of use wherein any arm can be selectively attached to a common extension arm and conjoined using a locking mechanism.

A still further object of the invention is to provide a self-retaining retractor and method of use that minimizes the number of practitioners.

Another object of the invention is to provide a self-retaining retractor and method of use which reduces fatigue and risk of injury to practitioners who might otherwise be directed to use conventional retractors.

Another object of the invention is to provide a serf-retaining retractor that includes a surgical instrument holder, such as an endoscope holder.

An object of the invention is to provide a self-retaining retractor and method of use for repair of tendons.

Another object of the invention is to provide a self-retaining retractor and method of use for posterior surgical reconstruction of the lateral knee.

A further object of the invention is to provide a self-retaining retractor and method of use for surgical repair of distal ulnar fractures.

Yet another object of the invention is to provide a self-retaining retractor and method of use for surgical repair of lateral malleolus fractures.

Still yet another object of the invention is to provide a self-retaining retractor and method of use for surgical repair of metatarsal fractures.

Another object of the invention is to provide a self-retaining retractor and method of use for surgical repair of metacarpal fractures.

Another object of the invention is to provide a self-retaining retractor and method of use for veterinary surgical procedures.

The above and other novel features of the present invention will become apparent to those of ordinary skill in the art upon further reviewing and understanding the following detailed description and accompanying drawings. It is intended that additional organizations, methods of use and operation, features, objects, embodiments, and or advantages ascertained by one skilled in the art be included within the specification, the scope of the invention, and protected by the claims.

BRIEF DESCRIPTION OF THE DRAWINGS

The invention may take form in various components and arrangements of components, and in various steps and arrangements of steps. The drawings are only for purposes of illustrating embodiments and are not to be construed as limiting the invention.

DETAILED DESCRIPTION OF THE INVENTION

Figure 1:
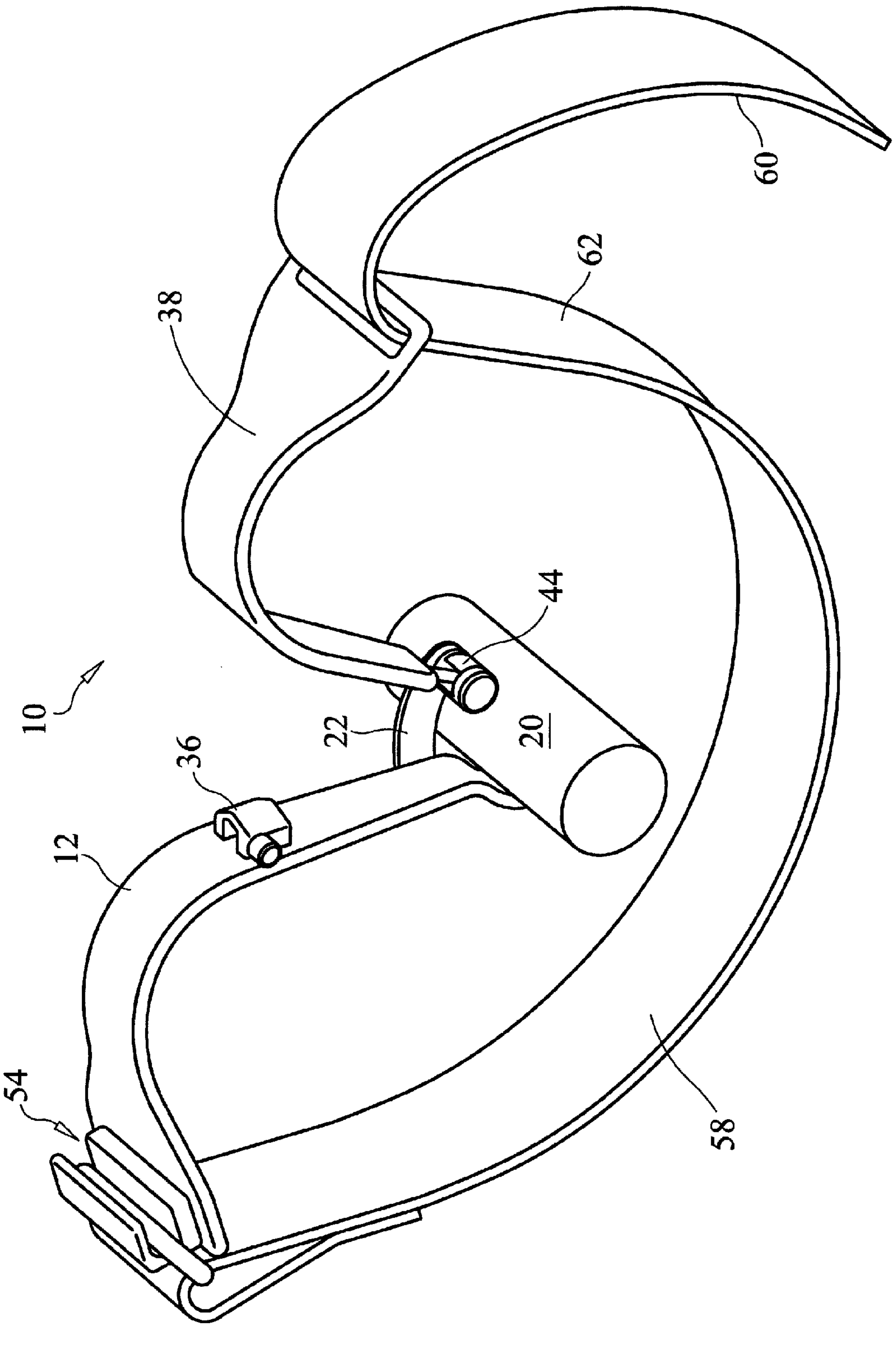
FIG. 1 is a perspective view of an embodiment of the invention in use.
Figure 2:
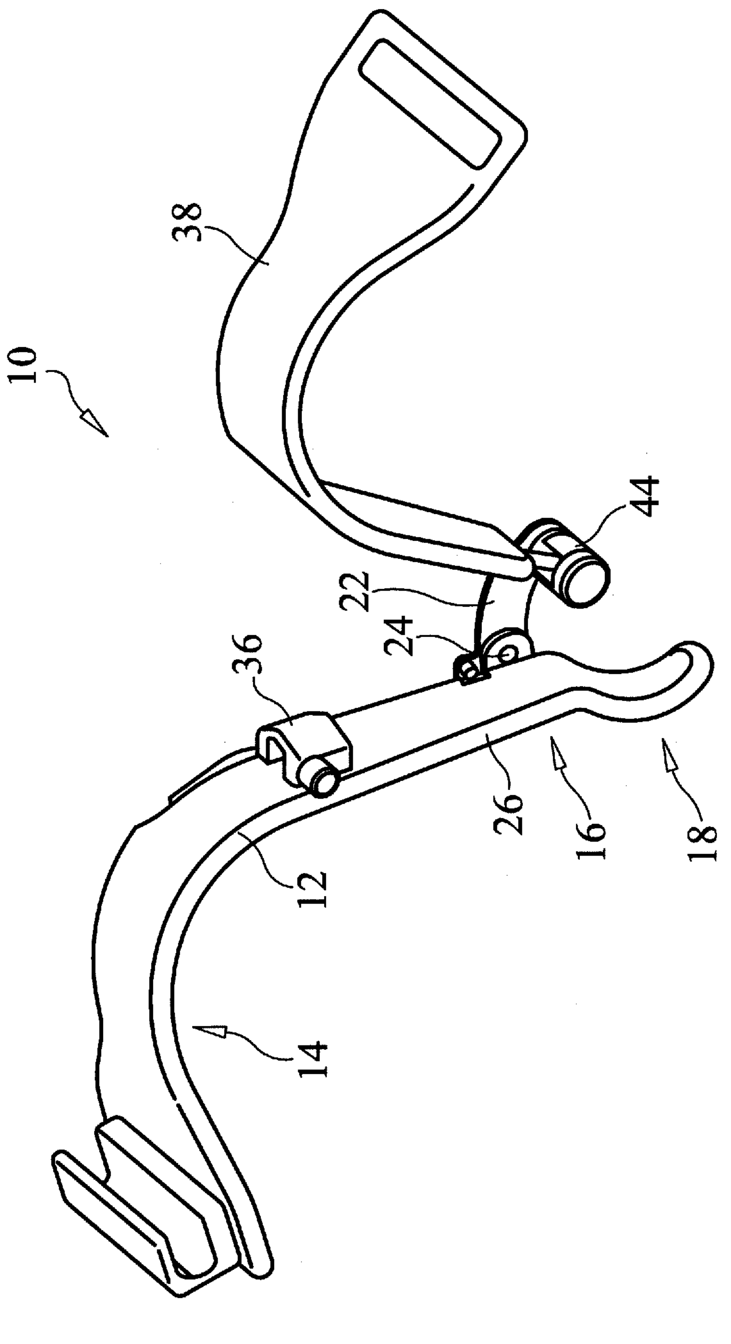
FIG. 2 is a perspective view of an embodiment of the invention in the deployed position.

With reference to FIGS. 1-5, in accordance with an embodiment of the invention, there is disclosed a medical device 10 for retraction of tissue for a surgical procedure, while in an open position or operative state. As shown in FIG. 1-5, the device 10 comprises a medial arm 12 having a first end 14 and a second end 16. The second end comprises a curved region 18. The curved region may be shaped like that of a Hohmann retractor, or other shape suitable for the purpose of the retraction. In one embodiment, as shown in FIG. 1, the curved end 18 is capable of being placed below a bone 20, such as the radius. Medial arm 12 is connected to an extension arm 22 by a rotatable connection 24 such as a hinge joint. The rotatable connection 24 allows the extension arm 22 to be selectively positioned about the axis of rotation. The rotatable connection 24 may be a pivot or any removable or permanent, fixed or variable connection means that provides for a rotatable axis between medial arm 12 and extension arm 22 and allows for freedom of positioning of the extension arm 22 during deployment of the device 10 or during a procedure.

As shown, in FIGS. 3-7, the rotatable connection 24 between the medial arm 12 and the extension arm 22 may include a locking mechanism 26. In one embodiment, the locking mechanism 26 may include a gap 28 between protrusions 30 on the rotatable connection 24 for inclusion of a locking pin 32. The locking mechanism may also include a guide 34 for the locking pin located on the medial arm 12. The guide 34 may be a hypotube or the equivalent, and may be used to hold the locking pin 32. The locking pin may be a K-wire or the equivalent. Other locking mechanisms known in the art are also contemplated.

The device 10 may also include at least one surgical instrument holder 36 located on the medial arm 12. The surgical instrument holder 36 may be bracket clamped to the medial arm receiving a locking pin, a tapered bracket, a clip, hook and loop fastener or an equivalent holder. The holder 36 may be for an endoscope or other instrument needed for surgery. The holder 36 may be selectively positioned longitudinally and laterally about medial arm 12 and may also be capable of rotating or swiveling about medial arm 12 depending on the instrument to be held or needs of a user. As shown, the holder 36 may be connected to medial arm 12 by a clamping device. A plurality of holders 36 may be disposed on the medial arm 12 or elsewhere on the device 10 and configured to support a plurality of instruments depending on the instruments being held or needs of a user.

Figure 8:
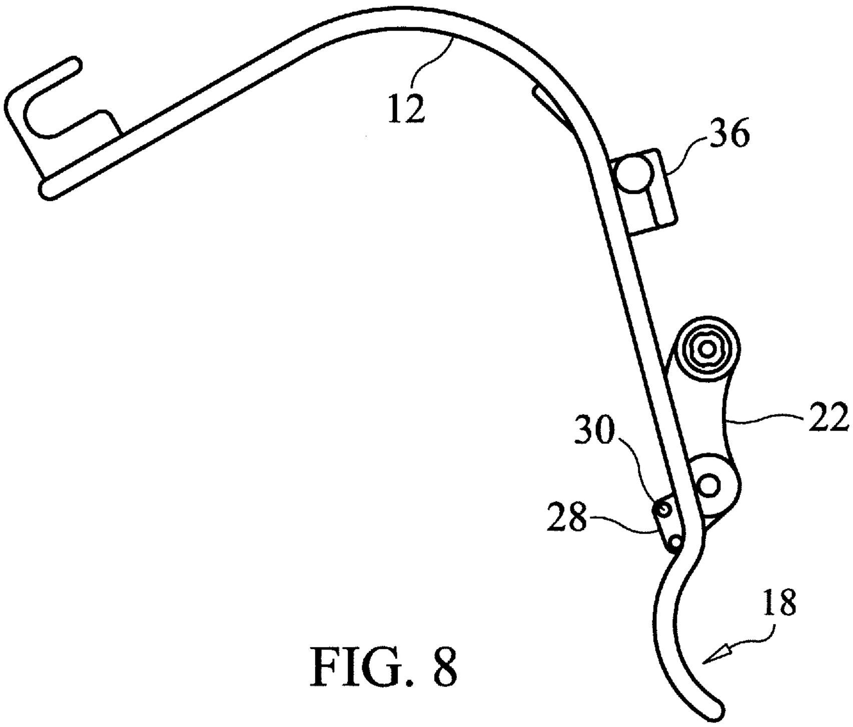
FIG. 8 is a front plan view of another embodiment of the invention in the undeployed position.
Figure 9:
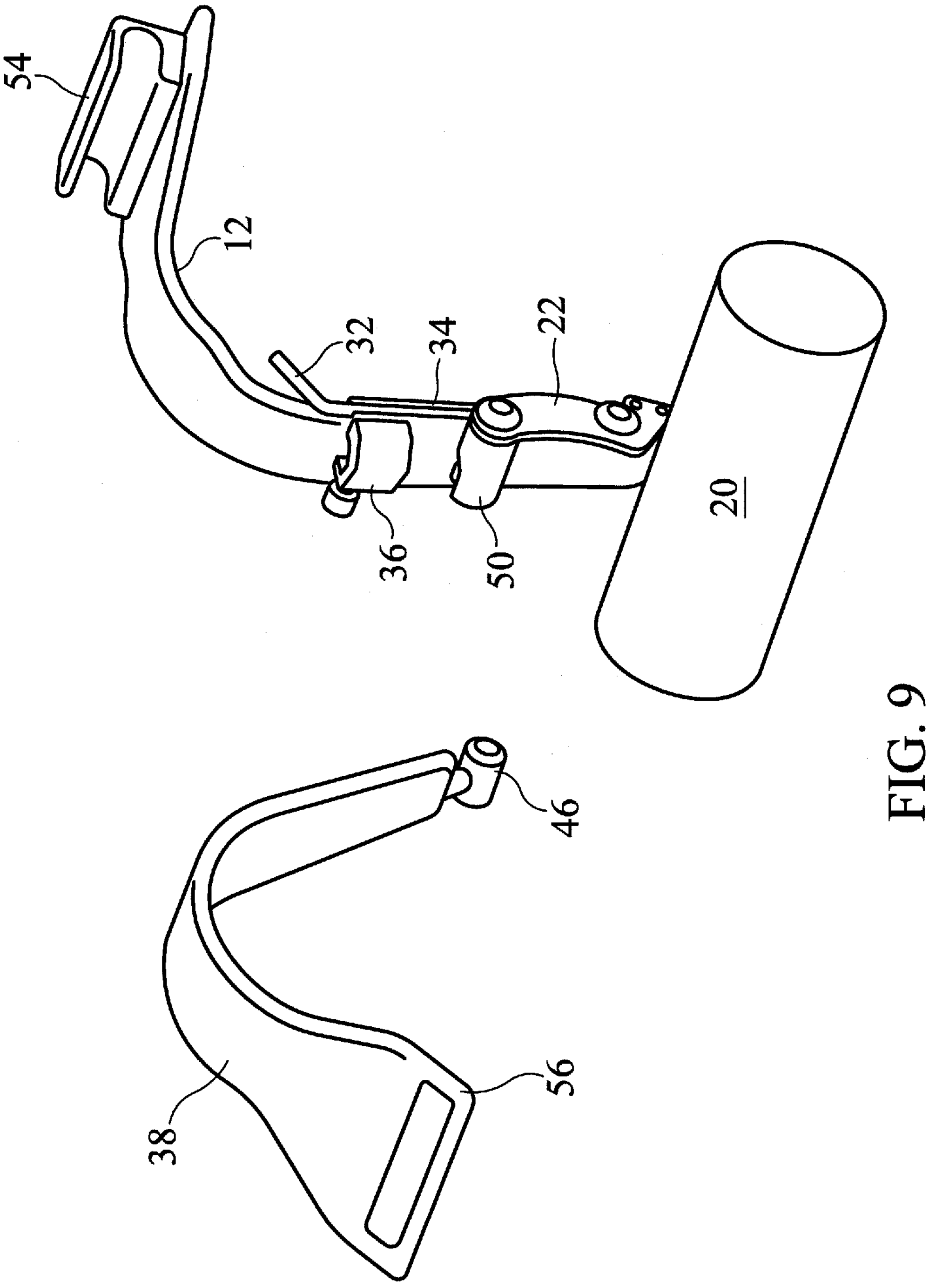
FIG. 9 is a partially exploded perspective view of another embodiment of the invention in use in the undeployed position.
Figure 10:
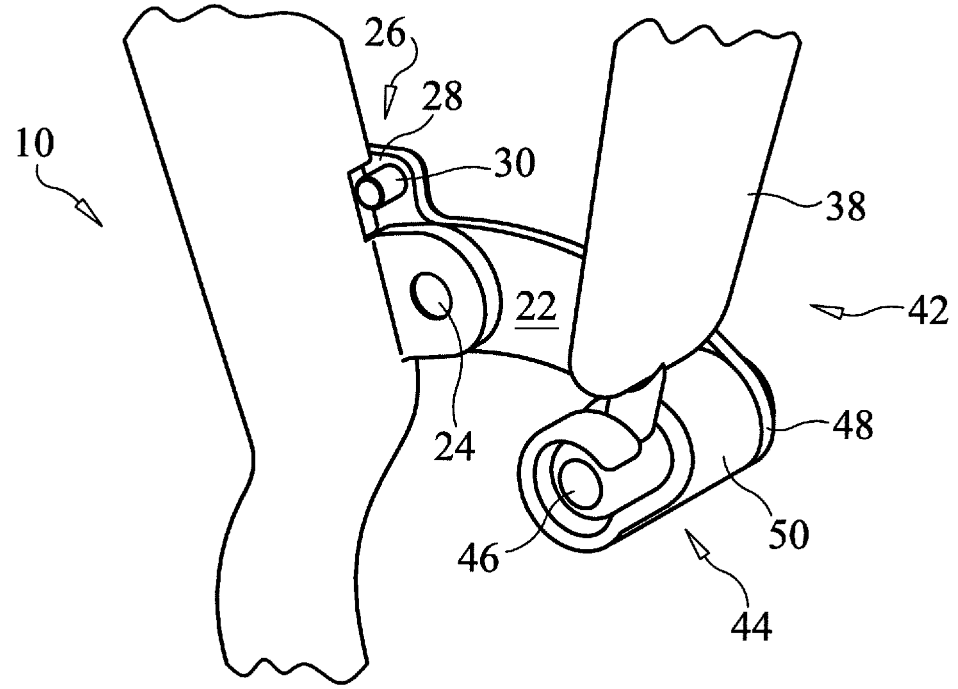
FIG. 10 is a detail view of the connection of the medial arm and the extension arm and the connection between the extension arm and the lateral arm of an embodiment of the invention.
Figure 11:
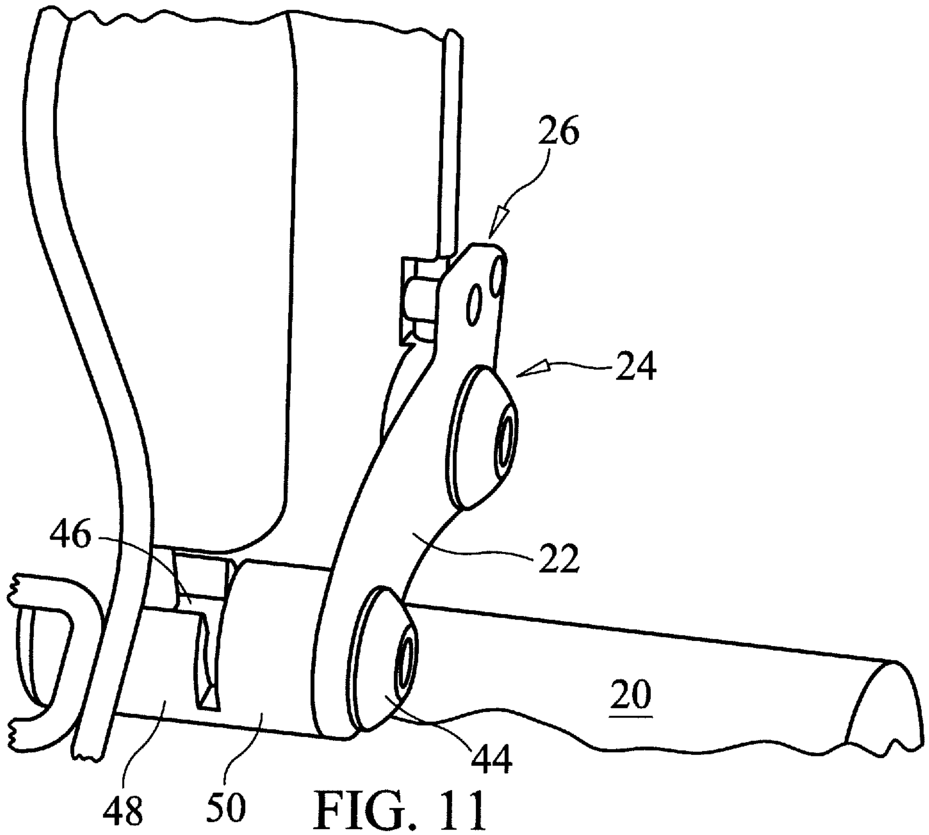
FIG. 11 is a reverse detail view of the connection of the medial arm and the extension arm and the connection between the extension arm and the lateral arm of an embodiment of the invention.

The device 10 also includes a lateral arm 38 having a near end 40 and a far end 42 that may have a connection 44 with the extension arm 22. As shown in FIGS. 1-4 and 8-9, the connection 44 between the lateral arm 38 and the extension arm 22 may be removable so that the lateral arm 38 may be attached to or removed from the extension arm 22 at the time of the user's choosing. FIG. 8 illustrates the device 10 showing the extension arm 22 in an undeployed position wherein the lateral arm 38 is removed. As shown in FIGS. 9-11, the connection 44 may comprise a pin-and-slot joint. For example, the lateral arm 38 may have a pin 46 insertable into a slot 48 located on a projection 50 on the extension arm 22. As shown, the slot 48 may be L-shaped. Alternatively, the connection 44 may be a snap-joint. Other equivalent means of making the connection are also contemplated.

Figure 12:
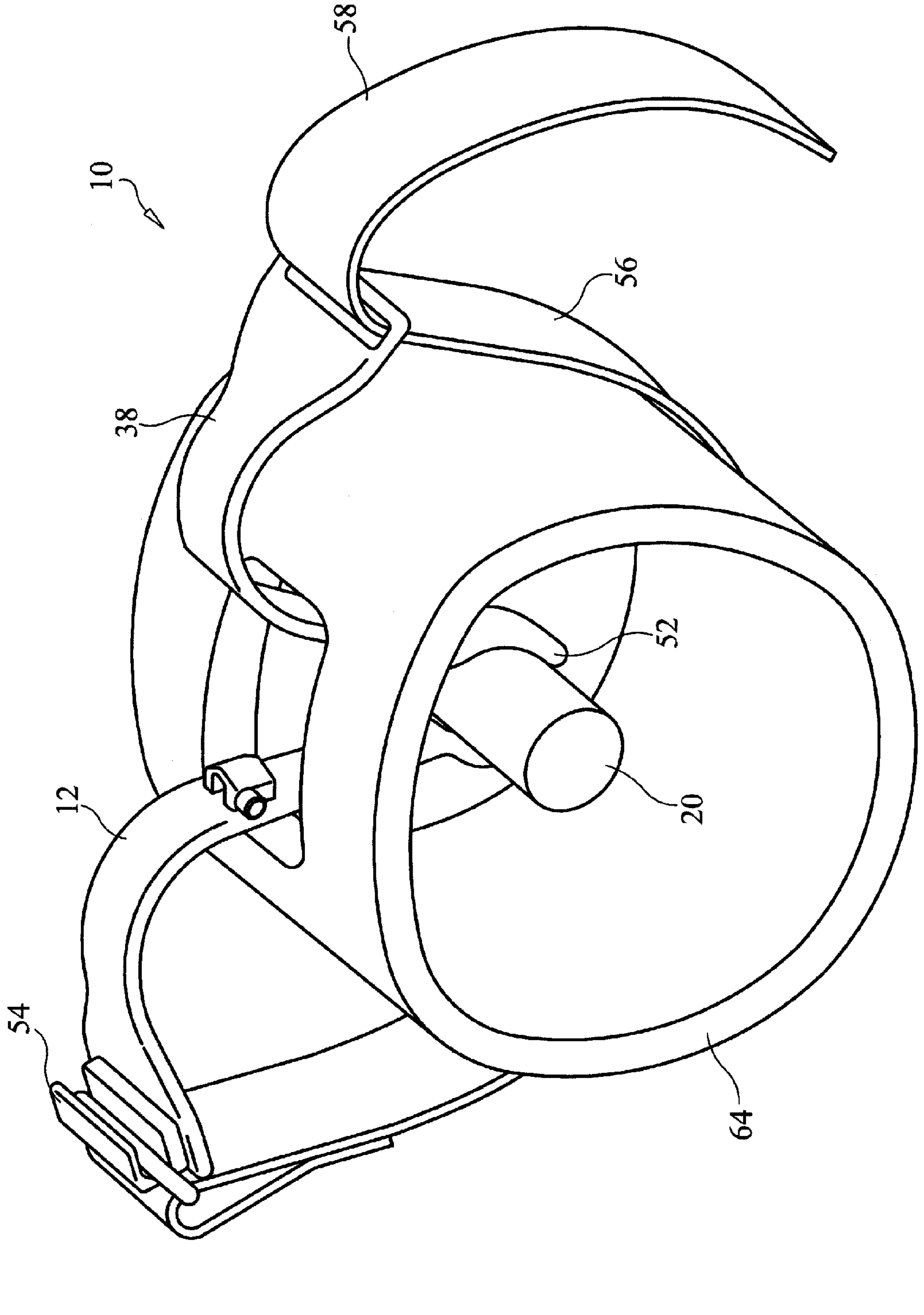
FIG. 12 is a perspective view of another embodiment of the invention.

In an alternative embodiment, as shown in FIG. 12, the far end 42 of the lateral arm 38 may further comprise a curved region 52. Like the curved region 18 of the medial arm 12, the curved region 52 of the lateral arm 38 may be similar to the curved portion of a Hohmann retractor, or of another shape suitable for the needs of the user.

In another embodiment, the lateral arm includes a holder for a surgical instrument, such as an endoscope. The holder on the lateral arm may be as described for the embodiment having a holder on the medial arm.

In an alternative embodiment shown in FIGS. 1, 9 and 12, the first end 14 of the medial arm 12 may include a first band connector 54 and the near end 40 of the lateral arm 38 may include a second band connector 56. As shown, the first band connector may be a slot adapted for receiving a loop for a band or strap 58 and the second band adapting receiving the band or strap so that the strap is tightenable around the portion of the body that receives the incision and the retraction for the procedure. As shown in FIG. 1, the strap may also be secured to itself by complementary hook 60 and loop 62 fastener regions. The strap may alternatively be secured with a buckle or equivalent method. Other means for securing the device 10 and holding a band or strap are also contemplated. In addition, as shown in FIG. 12, the device 10 may include a cuff 64 to aid in the isolation of the retracted area.

Figure 3:
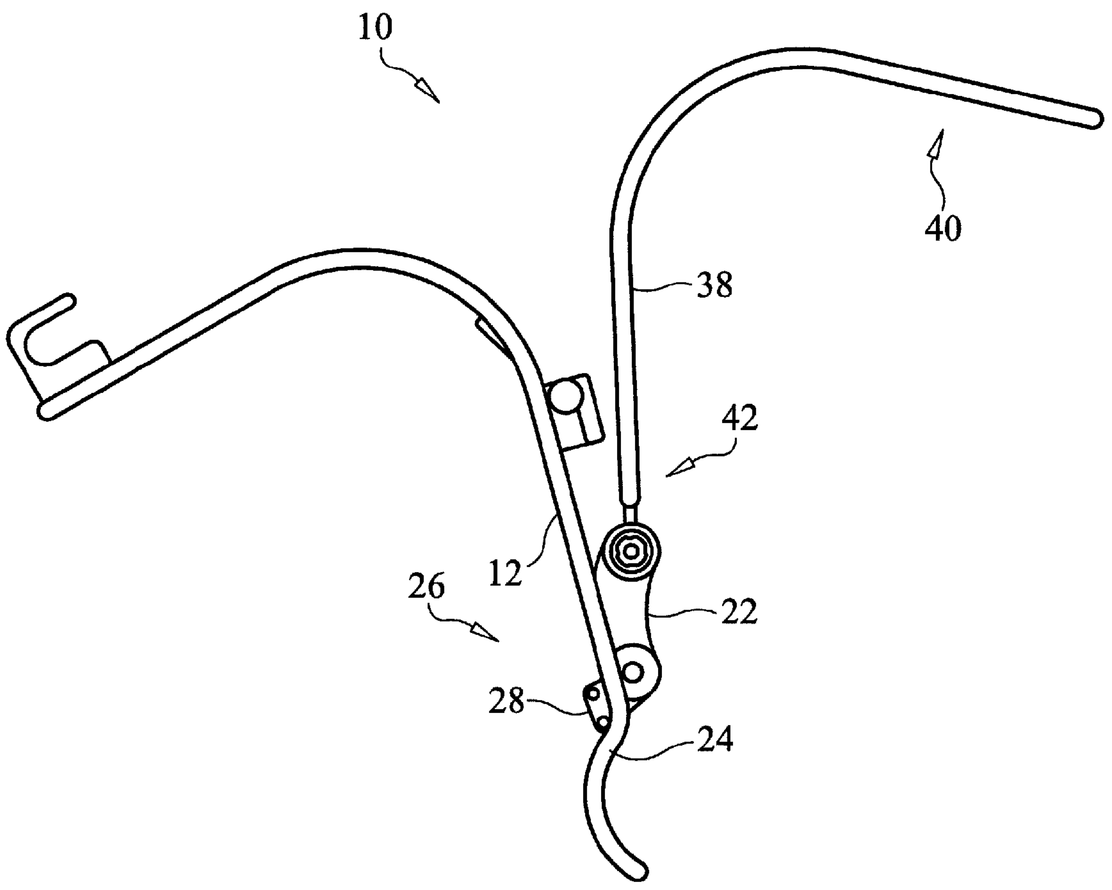
FIG. 3 is a front plan view of an embodiment of the invention in the undeployed position.
Figure 4:
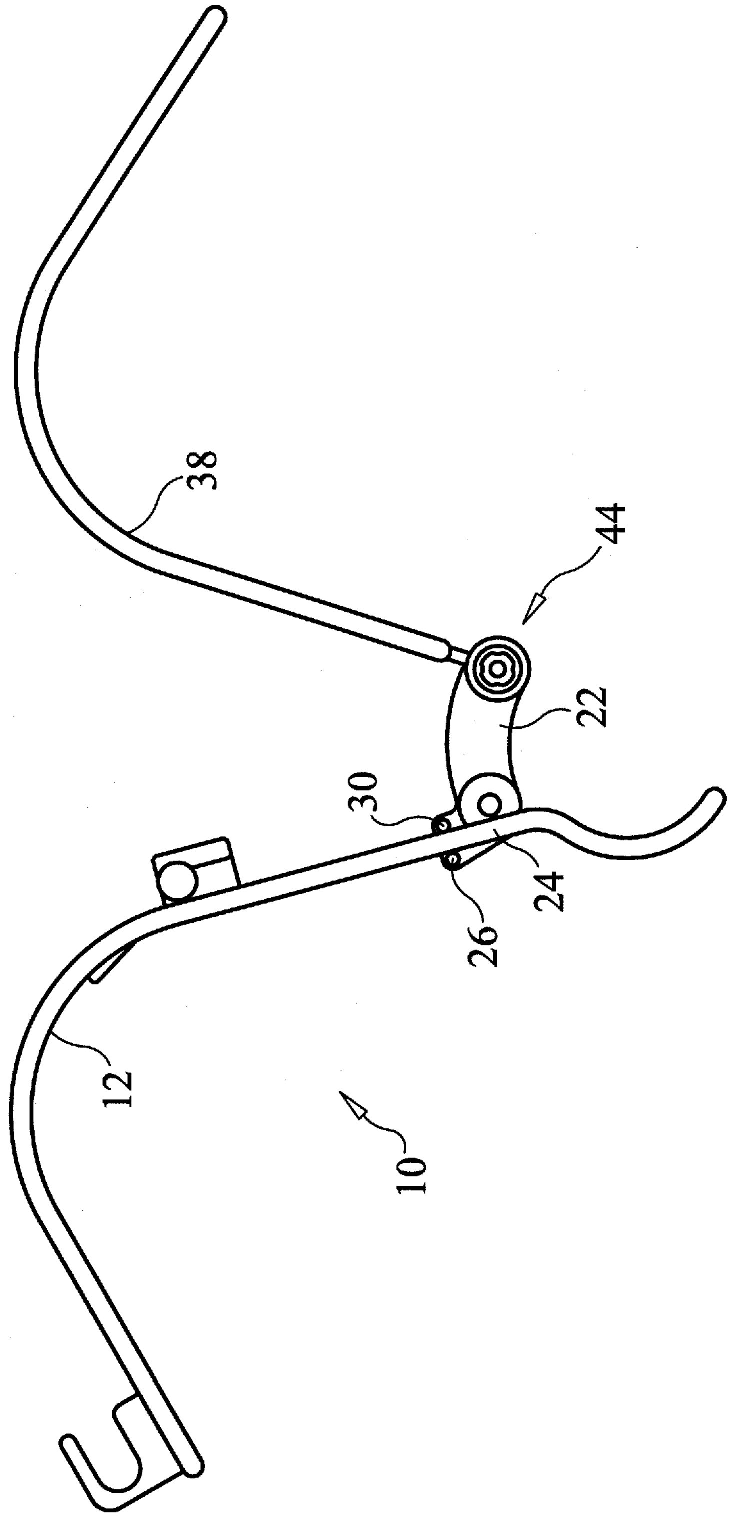
FIG. 4 is a front plan view of an embodiment of the invention in the deployed position.
Figure 5:
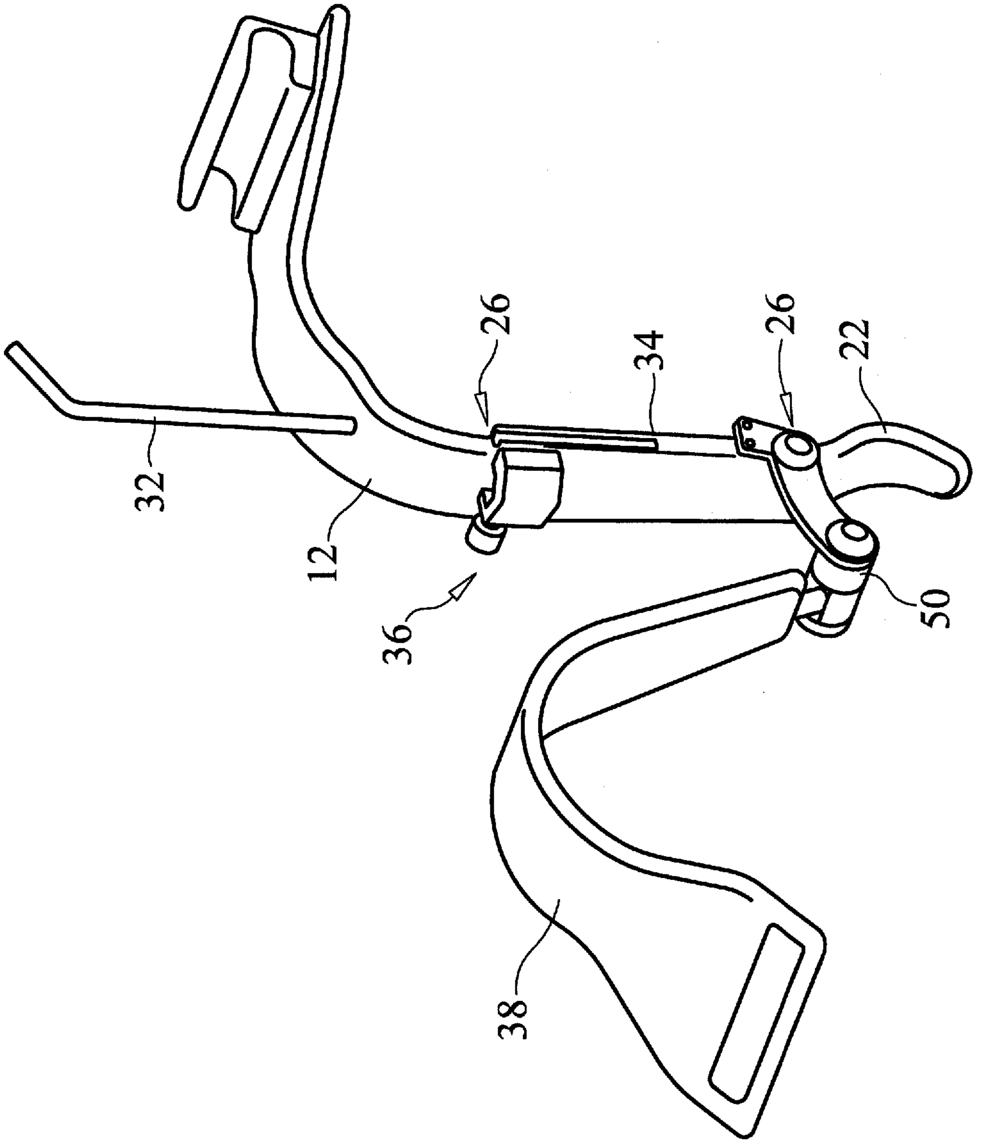
FIG. 5 is a partially exploded perspective view of an embodiment of the invention in the deployed position.
Figure 6:
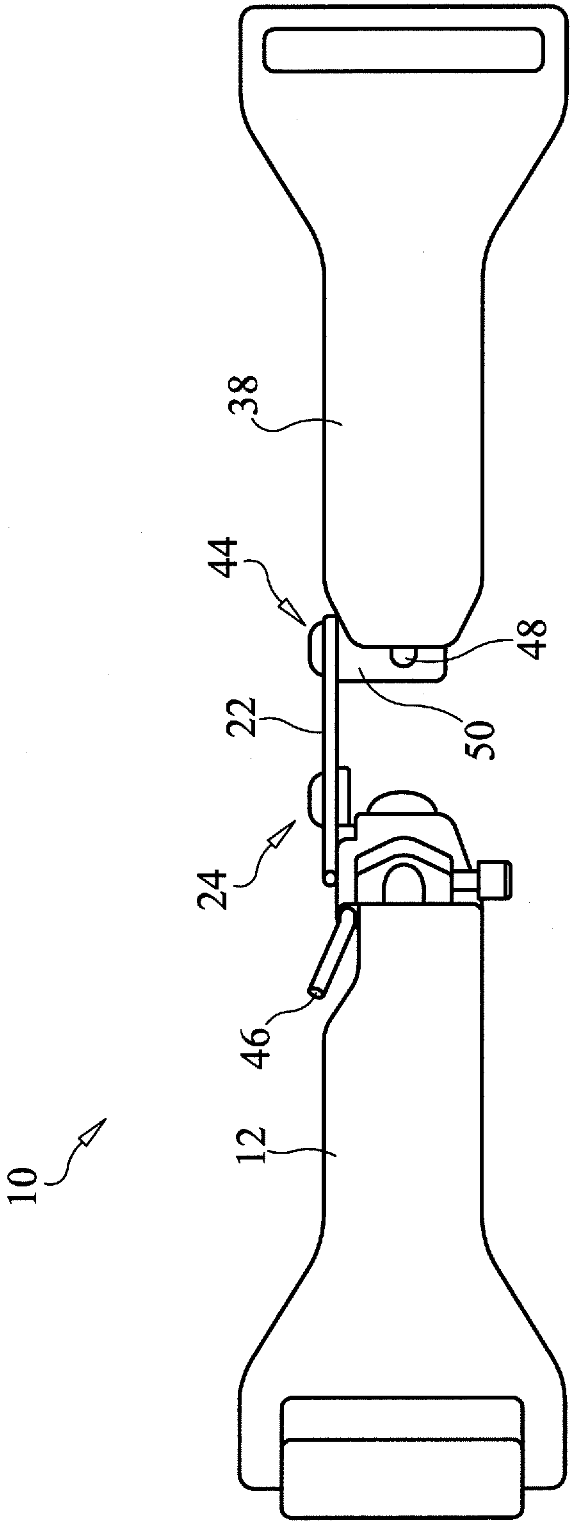
FIG. 6 is a top view of an embodiment of the invention in the deployed position.
Figure 7:
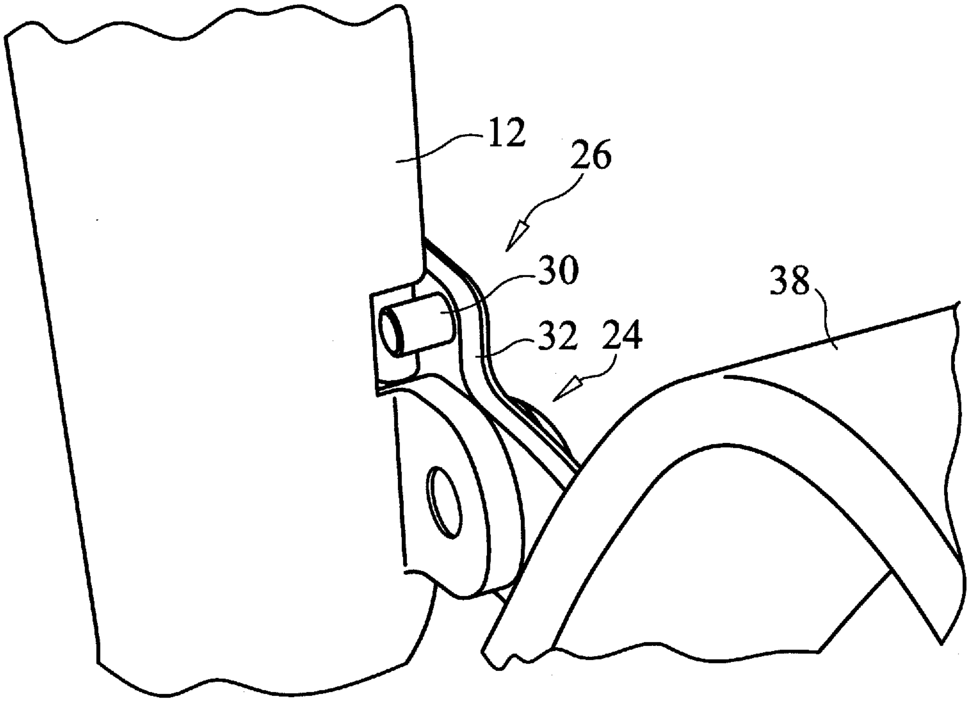
FIG. 7 is a detail view of the connection of the medial arm and the extension arm and the locking mechanism of the invention in the deployed position.

The method of the invention as used is described as follows. The device is introduced into an incision with the medial arm and the extension arm in the undeployed position as shown in FIG. 3. Alternatively, the device may be introduced with the extension arm in the undeployed position with the lateral arm detached from the extension arm as shown in FIG. 7. The curved portion of the device may then be placed under a bone accessible through the incision. Then the lateral arm may be connected with the extension arm. The extension arm may then be extended into the deployed position. The extension arm may then be locked by a locking mechanism. Then a band, strap or other tightening mechanism attached to the medial arm and the lateral arm may be tightened.

It will be appreciated by persons skilled in the art that the present invention is not limited to what has been particularly shown and described herein above. In addition, unless mention was made above to the contrary, it should be noted that the accompanying drawings are not to scale. A variety of modifications and variations are possible in light of the above teachings without departing from the scope and spirit of the invention

What is claimed is:

1. A medical device, comprising:

a body element selectively transitionable from a first geometric configuration to a second geometric configuration, the body element having a medial arm having a first end and a second end, wherein the second end is a curved Hohmann retractor end;

a lateral arm having a near end and a far end; and an extension arm in lockable, hinged connection to the medial arm, capable of hinged connection with the far end of the lateral arm, wherein the hinged connection is located at a proximal end of the extension arm and at a point proximate to the second end of the medial arm, and wherein extension of the extension arm transitions the body element from a first geometric configuration to a second geometric configuration, and wherein the hinged connection between the extension arm and the lateral arm is removable, and wherein the connection with the lateral arm may be made after the medial arm is deployed.

2. A medical device, comprising:

a body element selectively transitionable from a first geometric configuration to a second geometric configuration, the body element having a medial arm having a first end and a second end, wherein the second end is a curved Hohmann retractor end;

a lateral arm having a near end and a far end; and an extension arm in lockable, hinged connection to the medial arm, capable of hinged connection with the far end of the lateral arm, wherein the hinged connection is located at a proximal end of the extension arm and at a point proximate to the second end of the medial arm, and wherein extension of the extension arm transitions the body element from a first geometric configuration to a second geometric configuration, and wherein the hinged connection between the extension arm and the lateral arm is removable, and wherein the connection with the lateral arm may be made after the medial arm is deployed, further comprising a first tightening element connector located on the first end of the medial arm; and a second tightening element connector located on the near end of the lateral arm.

* * * * *